(12) United States Patent
Rapier et al.

(10) Patent No.: US 9,416,394 B2
(45) Date of Patent: Aug. 16, 2016

(54) PERICARP DNA EXTRACTION AND MATRILINEAGE DETERMINATION

(71) Applicant: AGRIGENETICS, INC., Indianapolis, IN (US)

(72) Inventors: Brandon Rapier, Zionsville, IN (US); Amy Pierce, Carmel, IN (US); Jennifer Hamilton, Indianapolis, IN (US); Ana Paula Canu, Colon Plant (AR); Juan Pablo Raimondi, Colon Plant (AR); Thomas G. Patterson, Westfield, IN (US); Nitigna Heath, Indianapolis, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 51 days.

(21) Appl. No.: 13/763,098

(22) Filed: Feb. 8, 2013

(65) Prior Publication Data

US 2013/0210006 A1 Aug. 15, 2013

Related U.S. Application Data

(60) Provisional application No. 61/597,013, filed on Feb. 9, 2012.

(51) Int. Cl.
| | | |
|---|---|---|
| *C12Q 1/24* | (2006.01) | |
| *C12Q 1/68* | (2006.01) | |
| *C12N 15/10* | (2006.01) | |

(52) U.S. Cl.
CPC .............. *C12Q 1/24* (2013.01); *C12N 15/1003* (2013.01); *C12Q 1/686* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2,472,971 A | 6/1949 | Hansen | |
| 6,254,914 B1 | 7/2001 | Singh et al. | |
| 6,899,910 B2 | 5/2005 | Johnston et al. | |
| 7,141,260 B2 | 11/2006 | Cope et al. | |
| 7,452,425 B1* | 11/2008 | Langhauser | 127/40 |
| 7,858,140 B2 | 12/2010 | Paustian et al. | |
| 2004/0043117 A1* | 3/2004 | Cope et al. | 426/238 |
| 2005/0025868 A1 | 2/2005 | Karl et al. | |
| 2006/0251764 A1* | 11/2006 | Abbas et al. | 426/53 |
| 2011/0078819 A1 | 3/2011 | Bullock | |
| 2011/0107453 A1 | 5/2011 | Milach et al. | |

FOREIGN PATENT DOCUMENTS

| | | | |
|---|---|---|---|
| EP | 1668127 A1 | 6/2006 | |
| WO | WO 2007/092131 | * | 8/2007 |

OTHER PUBLICATIONS

EC 3.2.1.3 (last viewed on Feb. 17, 2015).*
Misra et al., Glutamine Metabolism in Corn Kernels Cultured In Vitro., Plant Physiol. (1985), vol. 77, pp. 520-523.*
Kim et al. Enzyme Catalyzed Diusassembly of Corn Kernels., CUTC Conference, Indiana Corn Growers, Indianapolis, IN, Jun. 4-6, 2012.*
Dien, Bruce S., et al., "Hydrolysis and fermentation of pericarp and endosperm fibers recovered from enzymatic corn dry-grind process," Cereal Chem., 2005, pp. 616-620, vol. 82, No. 5.
Mistry, A.H. et al. "Alkali Debranning of Corn to Obtain Corn Bran," Cereal Chemistry, 1992, pp. 202-205, vol. 69 No. 2.
Shandera, D.D.L.et al. "Effect of Corn Wet-Milling Conditions (Sulfur Dioxide, Lactic Acid, and Steeping temperatures on Starch Functionality," Cereal Chemistry, 1996, pp. 632-637, vol. 73 No. 5.
Wolf, M.J., et al. "Amylose Determination in Dimethyl Sulfoxide Extracts of Maize," Cereal Chemistry, 1970 pp. 437-446, vol. 47, No. 4.
Singh, S.K. et al. "Effect of Sodium Hydroxide, Calcium Hydroxide, and Potassium Hydroxide on Debranning of Corn," Cereal Chemistry, 1997, pp. 254-257, vol. 74, No. 3.
Wang, Y. et al. "Effect of Pericarp Removal on Properties of Wet-Milled Corn Starch," Cereal Chemistry, 2006, pp. 25-27, vol. 83, No. 1.
Search Report and Written Opinion for International Application No. PCT/USs2013/025358, issued May 15, 2013.

* cited by examiner

*Primary Examiner* — Alexander Kim
(74) *Attorney, Agent, or Firm* — Eric J. Kraus; Magleby Cataxinos & Greenwood

(57) ABSTRACT

Methods for separating pericarp tissue from surrounding tissues in grain are provided. Included are methods for isolation of high-purity pericarp DNA from a grain plant that reflects the genotype of the maternal parent of the grain plant, such that the isolated DNA may be used in a PCR-based genotyping assay.

19 Claims, No Drawings

PERICARP DNA EXTRACTION AND MATRILINEAGE DETERMINATION

CROSS-REFERENCE TO RELATED APPLICATION

This application claims the benefit of U.S. Provisional Patent Application Ser. No. 61/597,013, filed Feb. 9, 2012, the disclosure of which is hereby incorporated herein in its entirety by this reference.

FIELD OF THE DISCLOSURE

Embodiments herein relate to systems and/or methods for the separation and isolation of high-purity maternal DNA samples from the pericarp of a seed, for example, in plant breeding.

BACKGROUND

Cereal grains, such as corn, contain a tough outer layer of tissue called the pericarp that is primarily composed of fiber. Underneath the pericarp tissue is the nutrient-rich aleurone layer, starchy endosperm layer, and the germ (embryo), which is comparatively rich in protein and oil. In corn milling, the maize seed pericarp is approximately 5.9% of the seed by weight and contains roughly 4% protein and 0.9% oil. Since the pericarp contains the major fraction of the bran or fiber in grains, grains from which the pericarp specifically, or fiber generally, has been removed are known as "debranned" grains.

Plant pericarp tissue originates or derives from the mature ovule wall, and it constitutes the outermost tissue layer of a seed. For example, corn pericarp is the outer covering of the corn kernel. Pericarp generally comprises three distinct layers: the exocarp; the mesocarp; and the endocarp. Pericarp is produced as a byproduct of some processes. For example, corn pericarp tissue has traditionally been discarded as a byproduct of wet- and dry-milling procedures used to recover cornstarch for ethanol production. However, isolated pericarp tissue has many uses in both agricultural and industrial processes. For example, corn pericarp tissue has served as a key ingredient in the production of end products, such as corn fiber gum (an emulsifier and bulking reagent) and corn fiber oil (a nutraceutical).

The conventional separation of pericarp from other seed tissues generally proceeds by wet- or dry-milling. A wet-milling process typically begins with kernel softening in an acid steeping solution (e.g., lactic acid and sulfur dioxide) and proceeds by separation of the pericarp from the kernel (Shandera and Jackson (1986) Cereal Chem. 73:632-7) using mechanical action. The germ-free kernel is then coarsely ground into a slurry and screened through sieves to remove coarse corn fiber. The germ, which is lighter than water, is collected off of the surface of the slurry and subsequently purified to obtain corn bran containing, for example, about 91% dietary fiber. Mistry and Eckhoff (1992) Cereal Chem. 69:2296-303. In a dry-milling procedure, corn is adjusted to 20% moisture content and processed with a degerminator, so as to strip away pericarp tissue and leave intact endosperm tissue. The separated pericarp may subsequently be dried (e.g., for corn fiber oil extraction), while the starch-containing endosperm may be used, for example, in ethanol production.

Corn pericarp may also be conventionally isolated by alkali debranning and sonication. See, e.g., U.S. Pat. No. 2,472,971 (alkali debranning); Liu (2002) "Ultrasounds enhanced corn pericarp separation process," M.S. thesis, Dept. of Food Science, University of Arkansas: Fayetteville, Ark. (sonication); Yang and Seibenmorgen (2001) "Ultrasound processing of foods—A case study of corn component separation." ASAE Paper No. 026022, ASAE: St. Joseph, Mich. (sonication). In an alkali debranning method, the pericarp is isolated chemically by soaking in an alkaline solution (e.g., calcium hydroxide, potassium hydroxide, and sodium hydroxide) at temperatures from ambient to about 100° C. The alkali loosens the interconnecting protein matrix between the pericarp and the endosperm tissue, allowing for mechanical separation in a latter step. Sonication coupled to heat and a soaking reagent has also been shown to be effective for pericarp isolation, but the pericarp must be recovered quickly to avoid re-adhering of the protein matrix (which will occur within hours if the sonicated material is taken out of solution).

In addition to industrial uses, pericarp tissue may also be applicable in some genetic studies. The majority of genetic applications use whole seed or embryo tissue for DNA extraction. However, using such source material results in the isolation of DNA from tissues that are derived from both maternal and paternal genetic contributions. Conversely, pericarp tissue is derived from the mature ovule wall of the seed; it is derived from maternal tissue and comprises only maternal DNA. The isolation of DNA from pericarp tissue may thus be used in applications involving the analysis or use of maternal DNA, for example and without limitation, maternal lineage analysis; characterization of heterotic groups; development of phylogenetic trees; and marker assisted breeding practices (pericarp DNA genotyping applications offer the unique opportunity to evaluate the maternal genetics of a hybrid plant line). Identifying maternally-inherited genes and maternally-inherited chromatin may allow breeders to select progeny that are genetically similar (or dissimilar) to one parent or the other for reciprocal recurrent selection and test-crossing.

A higher degree of pericarp tissue purity is required for the use of this maternally-derived tissue in genetics, compared to its use in other applications. Thus, methods for isolating pericarp tissue for non-genetic uses may not be appropriate or adaptable to isolate pericarp for genetic applications. Contaminating endosperm, aleurone, and germ tissue must be removed from pericarp prior to DNA extraction, as even the smallest amount of contaminating DNA in a sample of pericarp DNA may render the sample useless or lead to erroneous or uninterpretable results. For at least this reason, plant geneticists are unlikely to accept a priori that a pericarp isolation method will be adequate for their purposes, absent some confirmation that the isolated pericarp sample is not contaminated by endosperm, aleurone, or germ tissue. In addition to the absence of other tissue from the pericarp, the purity of isolated pericarp DNA should be in the range of 1.8-2.0 (as measured by the $A_{260}/A_{280}$ absorption ratio) to ensure adequate results in downstream DNA analysis.

BRIEF SUMMARY OF THE DISCLOSURE

To conduct maternal genetic screening, pure pericarp tissue must be effectively separated and isolated from underlying kernel tissues prior to extraction of nucleic acid molecules. Described herein are systems and methods for isolating pericarp tissue from a seed sample (e.g., a single seed and a plurality of seeds), as well as systems and methods for separating and extracting a high-quality nucleic acid molecule sample from pericarp tissue (e.g., maize pericarp tissue) that may in some embodiments be suitable for use in genetic analysis, e.g., PCR-based maternal genotyping. Also described are methods for using information obtained by genetic analysis of high-quality pericarp nucleic acids isolated according to some embodiments, for example, in plant breeding and matrilineage analysis.

In particular embodiments, a method for isolating pericarp tissue from a seed sample may comprise soaking the seed sample in hydrogen peroxide ($H_2O_2$) and enzymatic treatment of the seed sample. In certain examples, a seed sample may be soaked, with or without agitation, in an aqueous solution comprising 5% $H_2O_2$. In some examples, an enzymatic treatment of a seed sample comprises treating the seed sample with a specific or non-specific enzyme that digests proteins, starch, or cellulose of the seed sample into component parts. Non-limiting examples of such enzymes include amylase; alpha-amylase; amyloglucosidase; Pronase® (Roche, Indianapolis, Ind.), Fermgen®; Fermenzyme®, and Stargen® (Genencor, Rochester, N.Y.). In certain examples, a seed sample may be treated with about 1 mg/mL Pronase® under conditions wherein the enzyme is active.

In some embodiments, a method for isolating pericarp tissue from a seed sample may further comprise, for example and without limitation, providing a seed sample from a plant of interest; washing a seed sample to remove associated chemicals and/or particulate material; manual dissection of a seed sample; sonication of a seed sample of interest; rinsing a seed sample (e.g., so as to remove solvent and/or enzymes); separating released pericarp from a debranned seed sample; and/or soaking a seed sample in a solvent.

In other embodiments, a method for separating and extracting a high-quality nucleic acid molecule sample from pericarp tissue may comprise providing an isolated pericarp tissue sample prepared from a seed sample according to specific embodiments disclosed herein, disruption or lysis of cells comprised within the isolated pericarp tissue, removal of membrane lipids from the resulting cellular material, and precipitation of nucleic acid molecules. In particular embodiments, a method for separating and extracting a high-quality nucleic acid molecule sample from pericarp tissue may further comprise, for example and without limitation, removal of proteins, salts, and/or RNA molecules from the precipitated nucleic acid molecule sample. In some examples, a method for separating and extracting a high-quality nucleic acid molecule sample from pericarp tissue may be performed utilizing a Qiagen MagAttract® DNA extraction robotic platform. In particular examples, the utilization of such a platform is carried out in a fully-automated manner.

Isolated pericarp nucleic acid samples obtained by systems and methods according to particular embodiments of the invention may be sufficiently free of non-pericarp-derived nucleic acids that they may be used in PCR-based genetic analysis techniques without amplification of non-pericarp genetic information. Such purity was not achievable using conventional pericarp separation and DNA extraction techniques.

In additional embodiments, a method for using information obtained by genetic analysis of high-quality pericarp nucleic acids may comprise the utilization of a PCR-based analysis technique (e.g., KASPar® analysis and TaqMan® analysis). Information thus obtained may be used in particular embodiments in applications including, for example and without limitation, to deduce the genotype of an unknown or unavailable maternal parent plant; to compare pericarp-derived genetic information with the genotype of a putative maternal parent plant; detection of genetic variation; cultivar identification and genotyping; quantification of genetic diversity; characterization of accessions in plant germplasm collections; single-locus pedigree analysis; and taxonomic studies.

In certain embodiments, information obtained by genetic analysis of high-quality pericarp nucleic acids may be used to inform and/or direct a plant breeding program. For example, such information may be used, for example and without limitation, to study the inheritance of maternally-derived traits; to correlate the expression of one or more trait(s) of interest in a hybrid plant with a deduced maternal parental genotype; and/or to confirm the purity of maternal lineage in seed produced by a plant of interest.

The foregoing and other features will become more apparent from the following detailed description of several embodiments, which proceeds with reference to the accompanying Tables.

DETAILED DESCRIPTION

I. Overview of Several Embodiments

Some embodiments include pericarp separation and DNA extraction systems and/or methods that may allow the provision of high-quality, amplifiable DNA from plant seed (e.g., maize seed), such that the DNA may be used, for example and without limitation, in PCR-based genotyping (e.g., KASPar® SNP genotyping applications). A robust system to separate pericarp from the remainder of a seed is necessary to minimize or eliminate the risk of paternal tissue contamination in downstream analyses of the pericarp DNA. Isolation of pure pericarp tissue is especially critical when using pericarp-derived DNA in genotyping applications to determine matrilineage, as most genetic applications are robust and sensitive enough to amplify even minute quantities of non-target DNA.

Conventional pericarp separation methods in maize and other crops were evaluated and found to not be effective in producing high quality, pure, maternally-derived DNA for genetic applications such as genotyping. The isolation of high quality, pure, maternally-derived DNA is not trivial, previous experiments suggest that while conventional separation and subsequent extraction of pericarp DNA from sunflower hull result in sufficient maternal DNA yields, the maternal DNA recovered by a conventional process was of insufficient purity for use in many genetics applications, such that paternal alleles were amplified and detected from the "maternal" DNA in SSR applications.

Next, a variety of wet-milling procedures used by the ethanol industry to isolate corn starch from pericarp were evaluated to determine whether they could be adapted to provide adequate separation and isolation methods for use of resulting pericarp DNA in genetics (e.g., genetic techniques comprising PCR amplification). These methods included acid steeping; alkali debranning; and sonication (with or without heat). While not all of the methods that were evaluated provided adequate separation and isolation, an adequate process to separate and extract DNA from maize pericarp was developed and validated, using 20 diverse maize hybrids of known origin. Using this process, pericarp DNA that reproducibly amplifies maternal alleles in downstream KASPar™ PCR has been extracted with no contamination from the paternal parent.

Methods according to some embodiments of the invention allow the practitioner to isolate high-purity maternal pericarp DNA from hybrid seed with unknown pedigrees. In specific examples, such high-purity maternal pericarp DNA may allow the practitioner to reconstruct the haplotype of an unknown parent. In geographies outside of the United States, the use of hybrid germplasm is sometimes applied with no legal limitations to create new sources of genetic diversity. By reconstructing the haplotype of an unknown parent of such a diverse plant, pericarp analysis may be used to identify the source of the new diverse germplasm, and thereby to enhance breeding practices (e.g., in maize), for example, by allowing the practitioner to conform to domestic laws and regulations in the United States while using the new diverse germplasm in a breeding program. Thus, genetic analysis of pericarp DNA may be used to guide breeding practices and develop new lines from a first germplasm that have improved agronomic characteristics in geographies that use a second germplasm as a source of diverse, yet locally-adapted, germplasm. Furthermore, the comparison of hybrid seed pericarp DNA and maternal DNA may be used by researchers in specific examples to infer the haplotype of an alternative parent by assigning all non-maternal alleles to that of the alternate parent. This information can then be used in a predictive model to select germplasm from a similar genetic background for breeding and drive development of new hybrids with improved heterosis.

In addition to the analysis of hybrid materials, genetic analysis of pericarp DNA isolated and purified by methods according to some embodiments has several other potential applications. For example, a practitioner may evaluate pericarp DNA from a crop sample to determine if an entity is illegally using proprietary germplasm. Pericarp DNA may also be used as a genetic tool to determine if variation observed in early generation inbred lines is associated with maternal genetics. Also, when a maternally-inherited trait shows variability in field testing, pericarp DNA from individuals displaying the opposing phenotype may be compared with pericarp DNA from individuals displaying the trait to determine if the effect is associated with unique maternal alleles. Furthermore, pericarp DNA may be analyzed to determine if individuals or groups of seed descend from the same maternal lineage, which information may be useful when testing for potential line contamination in a previous generation. Overall, pericarp DNA genotyping data—achievable using methods according to embodiments of the invention—may support both the troubleshooting efforts of plant breeders, and their decisions to proceed with variety development.

II. Abbreviations

DMSO dimethyl sulfoxide
DNA deoxyribonucleic acid
EtOH ethanol
$H_2O_2$ hydrogen peroxide
IPA isopropyl alcohol
KASPar® KBiosciences™ Competitive Allele-Specific PCR SNP genotyping system
MW molecular weight
QTL quantitative trait locus
SDS sodium dodecyl sulfate
SNP single nucleotide polymorphism
SSR single sequence repeat III. Terms In the description and tables which follow, a number of terms are used. In order to provide a clear and consistent understanding of the specification and claims, including the scope to be given such terms, the following definitions are provided:

Pericarp tissue: The mature ovarian female tissue of the seed. Also referred to as coarse corn fiber, bran, hull, seed coat, or fiber. Composed of cellulose, hemicellulose, and lignin. Functions to protect the endosperm and embryo from disease and moisture loss. Separation from the seed portion is typically performed by digesting away the interconnecting protein matrix with enzymatic or alkaline methods.

Backcrossing: Backcrossing methods may be used to introduce a nucleic acid sequence into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Isolated: An "isolated" biological component (such as a nucleic acid) has been substantially separated, produced apart from, or purified away from other biological components in the cell or tissue of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules that have been "isolated" include nucleic acid molecules that have been separated or purified away from other nucleic acid molecules from a different plant tissue, at least to the extent that other nucleic acid molecules are not effectively PCR-amplified from the purified sample.

Pronase: Pronase is a commercially-available mixture of proteinases isolated from the extracellular fluid of *Streptomyces griseus*. Pronase is non-specific, and it digests both denatured and native proteins into individual amino acids.

Genetic material: As used herein, the term "genetic material" includes all genes, and nucleic acid molecules, such as DNA and RNA.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified aim of either type of nucleotide. A "nucleic acid molecule" as used herein is synonymous with "nucleic acid" and "polynucleotide." The nucleotide sequence of a nucleic acid molecule is read from the 5' to the 3' end of the molecule by convention. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA5, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

A nucleic acid molecule may include naturally-occurring and/or modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially-duplexed, triplexed, hairpinned, circular, and padlocked conformations.

Genome: As used herein, the term "genome" refers to chromosomal DNA found within the nucleus of a cell, and also refers to organelle DNA found within subcellular components of the cell.

Sequence identity: The term "sequence identity" or "identity," as used herein in the context of two nucleic acid sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using default parameters. Nucleic acid sequences with even greater similarity to a reference sequence will show increasing percentage identity when assessed by this method.

Specifically hybridizable/specifically complementary: As used herein, the terms "Specifically hybridizable" and "specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than a 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects sequences that share at least 80% sequence identity): Hybridization in 5×-6× SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence are those nucleic acid sequences that hybridize under stringent conditions (e.g., the Moderate Stringency conditions set forth, supra) to the reference nucleic acid sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, two nucleic acid sequence molecules are said to exhibit "complete complementarity" when every nucleotide of the sense strand read in the 5' to 3' direction is complementary to every nucleotide of the antisense strand when read in the 5' to 3' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

KBiosciences Competitive Allele-Specific PCR SNP genotyping system) (KASPar®: KASPar® is a commercially available homogeneous fluorescent system for determining SNP genotypes (KBiosciences Ltd., Hoddesdon, UK). A KASPar® assay comprises an SNP-specific "assay mix," which contains three unlabelled primers, and a "reaction mix," which contains all the other required components; for example, a universal fluorescent reporting system. In addition to these mixes, the user provides, inter alia, a FRET-capable plate reader, microtitre plate(s), and DNA samples that contain about 5 ng/L DNA.

A typical KASPar® assay comprises the steps of: allele-specific primer design (e.g., using PrimerPicker™, which is a free service available through the internet at the KBiosciences website); preparation of reaction mix including the allele-specific primers; admixing the reaction mix to DNA samples in a microtitre plate; thermocycling; reading the plate in a fluorescent plate reader; and plotting and scoring the fluorescent data. Data from each sample are plotted together on a 2-D graph, where the x- and y-axes correspond to FAM and VIC fluorescence values. Samples having the same SNP genotype cluster together on the plot (i.e., A/A; A/a; and a/a). More technical information about the KASPar® system, including a guide of solutions to common problems, is obtainable from KBiosciences Ltd. (e.g., the *KASPar® SNP Genotyping System Reagent Manual*).

Linked, tightly linked, and extremely tightly linked: As used herein, linkage between genes or markers may refer to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the terms "linked" may refer to a relationship between a marker and a gene, or between a marker and a phenotype.

Because the proximity of two genes or markers on a chromosome is directly related to the probability that the genes or markers will be passed together to individuals in the next generation, the term "linked" may also refer herein to one or more genes or markers that are located within about 2.0 Mb of one another on the same chromosome. As used herein, the term "tightly linked" may refer to one or more genes or markers that are located within about 0.5 Mb of one another on the same chromosome. And, as used herein, the term "extremely tightly linked" may refer to one or more genes or markers that are located within about 100 kb of one another on the same chromosome.

In view of the foregoing, it will be appreciated that markers linked to a particular gene or phenotype include those markers that are tightly linked, and those markers that are extremely tightly linked, to the gene or phenotype. Linked, tightly linked, and extremely tightly linked genetic markers of a phenotype may be useful in marker-assisted breeding programs to identify plant varieties comprising the phenotype, and to breed the phenotype into other varieties.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" refers to the version of the marker that is present in a particular individual. The term marker as used herein may refer to a cloned segment of DNA and may also or alternatively refer to a DNA molecule that is complementary to a cloned segment of DNA.

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. All above-described markers may be used in some embodiments of the present invention.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}P$. Other labels which may be used include, for example and without limitation: Fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait as the original marker.

A probe may be an exact copy of a marker to be detected. A probe may also be a nucleic acid molecule comprising, or consisting of, a nucleotide sequence which is substantially identical to a cloned segment of the subject organism's chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence. A probe may also be a nucleic acid molecule that is "specifically hybridizable" or "specifically complementary" to an exact copy of the marker to be detected ("DNA target").

Marker-assisted breeding: As used herein, the term "marker-assisted breeding" may refer to an approach to breeding directly for one or more traits. In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, a marker used in marker-assisted plant breeding is an SNP marker comprised within the maternal DNA of the pericarp of a seed.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

Seed sample: As used herein, the term "seed sample" may refer to one or more whole seeds or any material and/or substance obtained therefrom. For example, a seed sample may comprise one or more seeds from a plant of interest. A seed sample may also comprise a collection of seed tissues obtained from seed by a method according to embodiments of the invention, or by one or more steps in a method according to embodiments of the invention.

Unless specifically indicated or implied, the terms "a", "an", and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Isolation of Pericarp and Pericarp Nucleic Acids

Embodiments include systems and/or methods to isolate (i.e., extract, separate, and purify) pericarp tissue from a seed that is produced by a plant of interest. In some embodiments, the plant of interest may be a grain. In specific examples, the grain may be maize, wheat, rice, oats, barley, amaranth, sorghum, or other cereal grain. Embodiments include systems and/or methods that lead to the isolation of pericarp tissue that is significantly more pure (e.g., is contaminated with less non-pericarp material) than pericarp isolated according to a conventional process. In some examples, systems and/or methods according to embodiments of the invention may be used to isolate pericarp tissue of sufficient purity that DNA extracted therefrom may be used successfully in PCR-based analysis. For example, DNA extracted from the isolated pericarp tissue may be sufficiently free of non-pericarp DNA that a PCR protocol that amplifies alleles from the extracted pericarp DNA will not amplify alleles from non-pericarp DNA.

Embodiments include steps including, inter alia, soaking a seed sample in hydrogen peroxide ($H_2O_2$) and enzymatic treatment of the seed sample.

$H_2O_2$ may be utilized in embodiments of the invention to dissolve a protein matrix adhering the pericarp of a seed sample to non-pericarp tissues (i.e. aleurone layer; endosperm) of the seed sample. In particular examples, a seed sample may be soaked in an aqueous solution comprising up to 10% $H_2O_2$ at a 1:1 ratio of H2O2 to seed. For example, a seed sample may be soaked in an aqueous solution comprising about 1% $H_2O_2$; about 2% $H_2O_2$; about 3% $H_2O_2$; about 4% $H_2O_2$; about 5% $H_2O_2$; about 6% $H_2O_2$; about 7% $H_2O_2$; about 8% $H_2O_2$; about 9% $H_2O_2$; about 10% $H_2O_2$; and specific ranges including any or all of the foregoing (e.g., from about 3% to about 7% about 1% $H_2O_2$). In certain examples, a seed sample may be soaked in an aqueous solution comprising about 5% $H_2O_2$.

Enzymatic treatment may be utilized in embodiments of the invention, for example, to separate endosperm and/or embryonic tissue from the pericarp of a seed sample. In some examples, enzymatic digestion may be performed after an initial pericarp separation method (e.g., soaking in $H_2O_2$) is employed. Treatment of a seed sample with an enzyme may comprise incubating the seed sample in an aqueous solution comprising the enzyme and an appropriate buffer, at a temperature at which the enzyme is active.

A large number of specific and non-specific enzymes are known in the art to aid in the separation of tissues, for example, by digesting extracellular matrix proteins, starch (e.g., oligosaccharides and polysaccharides), or cellulose, and any such enzyme may be included in particular embodiments. Non-limiting examples of enzymes that may be used in some embodiments include amylase; alpha-amylase; amyloglucosidase; Pronase (Roche, Indianapolis, Ind.), Fermgen®; Fermenzyme®, and Stargen® (Genencor, Rochester, N.Y.). In certain examples, a seed sample may be treated with a non-specific protease (e.g., Pronase).

Pericarp samples are then incubated in a 1 mg/mL Pronase solution to remove residual endosperm minimizing the presence of endosperm and embryonic tissue contamination, which is partially paternal in origin.

In particular examples, an enzyme treatment comprises combining a seed sample (e.g., an initially-separated pericarp-containing seed sample) with a solution comprising a concentration of an enzyme that is sufficient to react with some, most, or essentially all, of the enzyme's substrate molecules in the seed sample. A solution comprising a particular enzyme will typically be buffered at a pH wherein the enzyme is active. For particular enzymes, the solution may be buffered at a pH of from about 4 to about 8. The "reaction mix" comprising the seed sample and the enzyme solution will typically be incubated at a temperature wherein the enzyme is active (e.g., between about 20° C. and about 60° C. (68° F. and about 122° F.) for particular enzymes) for a sufficient period of time for the amount of enzyme in the reaction mix to react with some, most, or essentially all, of the enzyme's substrate molecules in the seed sample. Particular reaction conditions will vary with the particular enzyme(s) being used, and their selection is within the discretion of the skilled practitioner. For example, certain examples comprising Pronase digestion of a seed sample comprise a reaction mix with 1 mg/mL Pronase at pH 7.5 and 40° C.

Methods according to particular embodiments may further comprise steps including, for example and without limitation, providing a seed sample from a plant of interest; washing a seed sample to remove associated chemicals and/or materials; manual dissection of a seed sample; sonication of a seed sample of interest; rinsing a seed sample (e.g., so as to remove solvent and/or enzymes); separating released pericarp from a debranned seed sample; and/or soaking a seed sample in a solvent. Solvents that may be used to soak a seed sample in particular embodiments include, for example and without limitation, an acidic solvent (e.g., a solvent comprising lactic acid); a basic solvent (e.g., a solvent comprising a hydroxide salt); water; an alcohol (e.g., EtOH); DMSO; and mixtures of any of the foregoing. Soaking of a seed sample may include mechanical agitation of the seed sample, for example and without limitation, by mixing of the sample or placement of the sample in the solution on a moving (e.g., rotating or shaking) surface.

For example, in some embodiments, soaking a seed sample in a solvent comprises adding water (the solvent) to grain (the seed sample) to form a grain-water mixture, and agitating the grain-water mixture to detach and/or release the pericarp from the remainder of the grain. In particular examples, prior to adding the water, the grain may have been soaked in a strong base, such that the grain has absorbed substantially all of the aqueous solution of strong base, or alternatively, the grain may have absorbed only a portion of the aqueous solution of the strong base. After soaking in a strong base, but before adding the water, the grain may be separated from the strong base. Addition of water may dilute a remaining portion of the strong base (e.g., an amount of the strong base remaining after separation of the grain from the strong base). Thus, in particular examples, a grain-water mixture to be agitated may contain some of an aqueous solution comprising a strong base.

In particular embodiments, soaking a seed sample in a solvent comprises adding water and an abrasive to a seed sample to form a seed sample-solvent abrasive mixture. An abrasive may be, for example and without limitation, sand; calcium carbonate; polypropylene shavings; ground corn cobs; iron filings; and/or alumina. In some examples, a seed sample-solvent abrasive mixture is agitated to detach and/or release the pericarp from the remainder of the seed sample.

Separating released pericarp from a debranned seed sample may comprise, for example and without limitation, contacting a mixture of pericarp and the remainder of a debranned seed sample from which the pericarp was released with a screen to separate the released pericarp from the debranned grain; by aspiration; density flotation; and/or by other methods known to those skilled in the art.

Some embodiments include systems and/or methods to isolate (i.e., extract, separate, and purify) nucleic acid molecules from the isolated pericarp of a seed that is produced by a plant of interest (e.g., a grain). In specific examples, the matrilineage of the plant of interest may be unknown. Once pericarp tissue has been isolated by a method according to an embodiment of the invention, any DNA extraction method known in the art may be used to isolate high-purity DNA from the pericarp tissue. A DNA extraction method utilized in some embodiments may include cell disruption or cell lysis (e.g., by grinding or sonicating the pericarp tissue); removal of membrane lipids (e.g., with a detergent); and precipitation of DNA (e.g., with cold EtOH or IPA). A DNA extraction method may also include removal of proteins from the sample; removal of salts from the sample; and/or removal of RNA molecules from the sample.

In particular examples, nucleic acid molecules are isolated from a pericarp tissue sample isolated by the foregoing systems and/or methods by DNA extraction using a Qiagen MagAttract® bead-based chemistry. In particular examples, DNA extraction using a Qiagen MagAttract® bead-based chemistry may be performed in a fully-automated manner, thereby significantly reducing the time and expense involved in the procedure.

Differences may exist between hybrid seed of various lineages with regard to seed coat thickness and/or the composition of the underlying cellular matrix joining pericarp and non-target seed tissues. Such differences may impact ease of pericarp isolation, and the quality and yield of DNA obtained therefrom by an extraction process. However, systems and methods according to some embodiments were exemplified and validated by extracting DNA from maize pericarp isolated from seeds produced by 20 maize hybrids, which were selected for their differences in seed coat thickness and cellular matrix composition. As demonstrated by the several examples detailed below, DNA obtained from these 20 diverse hybrid seed groups using systems and methods according to some embodiments exhibited a yield between 0.66 and 8.82 ng/μL, and a purity between 1.68 and 3.06 ($A_{260}/A_{280}$). Thus, embodiments are suitable for extracting high-quality pericarp DNA from seed samples exhibiting a wide range of seed coat properties.

Accordingly, pericarp DNA isolated according to some embodiments of the invention may be obtained in amounts between about 0.65 and about 9 ng/μL. For example, pericarp DNA may be isolated in an amount of at least 0.63; about 0.65; about 0.675; about 0.7; about 0.725; about 0.75; about 0.775; about 0.8; about 0.825; about 0.85; about 0.875; about 0.9; about 0.95; about 1; about 1.5; about 2; about 2.5; about 3; about 3.5; about 4; about 4.5; about 5; about 5.5; about 6; about 6.5; about 7; about 7.5; about 8; about 8.5; about 8.75; about 9; and less than 9.25 ng/μL, or values and ranges including any of the foregoing.

Pericarp DNA isolated according to some embodiments of the invention may be obtained with a purity between about 1.65 and about 3.1 $A_{260}/A_{280}$. For example, pericarp DNA may be obtained with a purity of at least 1.60; about 1.65; about 1.7; about 1.75; about 1.8; about 1.85; about 1.9; about 1.95; about 2.0; about 2.25; about 2.5; about 2.75; about 3.0; about 3.1; and less than about 3.5 $A_{260}/A_{280}$, or values and ranges including any of the foregoing.

Moreover, DNA isolated using systems and/or methods according to some embodiments may be distinguished from DNA isolated by conventional methods by its nearly homogeneous composition of pericarp DNA, which may allow PCR-based genetic analysis of pericarp DNA with a heretofore unobtainable ease and precision. Thus, in particular examples, a sample of isolated DNA obtained using systems and/or methods according to some embodiments may consist essentially of pericarp DNA (e.g., allelic information contributed to a hybrid from which the seed sample was obtained by the hybrid's paternal parent is not amplified by PCR from the sample of isolated DNA under conditions wherein allelic information from the maternal parent is amplified).

V. Determination of Matrilineage Through Analysis of Isolated Pericarp DNA

In some embodiments, high-quality pericarp DNA extracted from pericarp tissue that has been isolated from a seed sample using systems and/or methods according to this disclosure may be analyzed to determine at least a portion of the genotype of the maternal parent of the plant from which the seed sample was obtained. In particular embodiments, the genotype (or portion thereof) thus determined may be used to provide information about a plant of interest's maternal parent plant, when the maternal parent plant itself is unknown or not available for sampling or analysis.

Analysis of high-quality pericarp DNA extracted from pericarp tissue that has been isolated from a seed sample using systems and/or methods according to this disclosure may be performed utilizing any system or method of genetic analysis known in the art, for example and without limitation, PCR-based analysis techniques (e.g., KASPar® analysis and TaqMan® analysis). In some embodiments, high-quality pericarp DNA extracted from pericarp samples isolated according to the disclosure is of sufficient purity that PCR-based techniques may be used without resulting in amplification of trace paternal allelic information, which techniques were not possible using conventional pericarp tissue isolation techniques. In particular examples, a PCR-based genetic analysis of pericarp DNA is performed using the KASPar® SNP genotyping platform (KBioscience, Hoddesdon, UK). Target DNA sequences used to design molecular markers for PCR-based genotyping may be identified from genome databases, or through independent sequencing.

In some examples, a genotype of an unknown or unavailable maternal parent plant that has been deduced from pericarp DNA isolated from a seed sample using systems and/or methods according to this disclosure may be compared to the genotype of a putative maternal parent plant. In many circumstances, it may be important for the practitioner to confirm that a hybrid plant from which a seed sample has been obtained is not a progeny plant produced from a particular parent or germplasm. For example, it may be important to know that a particular hybrid plant is not a progeny plant produced from a maternal parent or germplasm that is the property of another entity or otherwise subject to breeding restrictions. Alternatively, it may be important for the practitioner to determine whether a particular hybrid is a progeny plant produced from a particular maternal parent or germplasm. For example, it may be important to determine whether a particular plant was produced from a plant or germplasm that is the property of the practitioner, e.g., to determine whether the practitioner's property has been or is being used unlawfully.

In some examples, pericarp DNA isolated from a seed sample using systems and/or methods according to this disclosure may be analyzed to deduce the genotype of an unknown or unavailable maternal parent plant. The genotype of a maternal parent may be determined for any reason for which such information may be desired, for example, to evaluate maternally inherited traits in populations with contrasting phenotypes. By way of further example, when a particular hybrid plant with an unknown or unavailable maternal parent exhibits one or more desirable traits, a plant breeder may desire to know the genotype of the plant's maternal parent, at least at QTLs that correspond to the one or more desirable traits or genetic markers that are linked to the one or more traits. In situations where the paternal parent plant of such a hybrid plant is known or available, the maternal genotype deduced by analysis of pericarp DNA isolated from the hybrid may be used to identify known or available plants of the same species that may be bred with the paternal parent to produce a second hybrid that has an increased likelihood of exhibiting the same desirable trait(s) as the first.

In addition to the foregoing, maternal genotyping may be determined for purposes including, for example and without limitation, detection of genetic variation; cultivar identification and genotyping; quantification of genetic diversity; characterization of accessions in plant germplasm collections; single-locus pedigree analysis; and taxonomic studies.

VI. Use of Isolated Pericarp DNA in Plant Breeding

In some embodiments, pericarp (maternal) genotypic information acquired utilizing systems and/or methods according to the disclosure may be used to inform and/or guide plant breeding decisions, e.g., as may be made while selectively breeding a plant for one or more traits of interest. For example, the inheritance of maternally-derived traits may be studied by correlating the pericarp genotypic information acquired from a particular hybrid with expression of the maternally-derived trait. By way of additional example, an unknown maternal parent plant may be crossed with a particular plant, e.g., to enrich the genetic diversity of the plant's germplasm, and/or to capture a new source of heterosis. In circumstances including the foregoing, pericarp genetic information may be used to deduce the haplotype of the unknown parent. This information may then be used to drive development of future breeding decisions.

In addition to the analysis of hybrid materials, genotypic information acquired utilizing systems and/or methods according to the disclosure may be used to determine the genetic purity of maternal lineage in seed being developed for breeding purposes. For example, in rare cases where unexpected phenotypes are observed in yield trials or late stages of the variety development process, pericarp DNA may be extracted and analyzed to determine whether contaminating pollen was introduced into development of the conversion in a previous generation. This information may be used to support both troubleshooting efforts and decisions regarding whether or not to proceed with the development of the variety exhibiting the unexpected phenotype.

The following examples are provided to illustrate certain particular features and/or embodiments. The examples should not be construed to limit the disclosure to the particular features or embodiments exemplified.

EXAMPLES

Combinations of various pericarp removal and purification techniques were studied to discover a robust pericarp DNA isolation method capable of providing high-purity DNA that could be used for PCR-based genetic analysis. The method discovered was validated across various maize germplasm via KASPar® SNP genotyping.

Example 1

Conventional Pericarp Removal Techniques Produce Pericarp Tissues that are Contaminated with Endosperm Tissues Seed from maize hybrids was obtained and used for development of the initial pericarp removal process. Prior to experimentation, each set of seed was rinsed twice with $diH_2O$ to wash away all the insecticide and fungicide, and tip caps were removed to initiate imbibition in the soaking reagent.

Pericarp separation methods that were evaluated, and the methods which failed to successfully disrupt the interconnecting protein matrix between the pericarp and endosperm are listed in Table 1.

TABLE 1

Seed separation methods tested that failed to loosen pericarp tissue from underlying endosperm. Ease of pericarp removal and pericarp intactness when removed were evaluation criteria.

| Soaking Reagent | Soak Time (min.) | Temp | Ease of Removal | Intactness |
|---|---|---|---|---|
| Water | 30 | Ambient | Difficult | Small pieces |
| Water | 60 | Ambient | Difficult | Small pieces |
| Water | 120 | Ambient | Moderate | Large pieces |
| Water | 960 | Ambient | Moderate | Small pieces |
| Water | 1440 | Ambient | Moderate | Large pieces |
| 70% EtOH | 30 | Ambient | Moderate | Large pieces |
| 70% EtOH | 60 | Ambient | Moderate | Large pieces |
| 70% EtOH | 120 | Ambient | Difficult | Large pieces |
| 70% EtOH | 240 | Ambient | Moderate | Large pieces |
| 3% $H_2O_2$ | 60 | Ambient | Moderate | Large pieces |
| 3% $H_2O_2$ | 180 | Ambient | Moderate | Large pieces |
| 5% $H_2O_2$ | 180 | Ambient | Moderate | Whole |
| 7% $H_2O_2$ | 60 | Ambient | Moderate | Large pieces |
| 7% $H_2O_2$ | 180 | Ambient | Moderate | Large pieces |
| Sulfur dioxide + lactic acid | 1440 | Ambient | Moderate | Large pieces |
| 5% $H_2O_2$ (two soaks) | 60 + 60 | Ambient | Moderate | Large pieces |
| 5% $H_2O_2$ (two soaks) | 120 + 120 | Ambient | Moderate | Large pieces |
| 5% $H_2O_2$ (three soaks) | 60 + 60 + 60 | Ambient | Moderate | Large pieces |
| 5% $H_2O_2$ (two soaks) | 300 + 300 | Ambient | Moderate | Large pieces |
| 1% lactic acid + 1 mg/mL pepsin | 1500 | 37° C. | Moderate | Large pieces |
| 90% DMSO (1/2 seed) | 1440 | Ambient | Difficult | Small pieces |
| Amylase + amyglucosidase | 1500 | 37° C. | Moderate | Large pieces |
| 3% $H_2O_2$ (hexane wash) | 60 | Ambient | Moderate | Large pieces |

Example 2

Isolation of Pericarp DNA Suitable for Use in PCR

Several non-enzymatic methods were found that successfully disrupted the interconnecting protein matrix between the pericarp and endosperm including: sonication in water for 30 min.; sonication in 6% NaOH for 8-10 min.; seed soak in 70% EtOH for 24 hrs.; and seed soak in 3-5% $H_2O_2$ for 1 hr. These four aforementioned methods were then paired with purification treatments (Table 2) aimed at removing extraneous endosperm tissue. For all reagent combinations, DNA from both hybrids was evaluated for yield, purity, quality, and paternal allele contamination. Using those criteria to guide the development process, it was discovered that a 5% hydrogen peroxide ($H_2O_2$) seed soak followed by a 24 hr. 1 mg/mL Pronase incubation at 40° C. was an effective method to prepare pericarp for DNA extraction and subsequent SNP genotyping, as described in further detail below.

TABLE 2

Summary of promising pericarp separation methods evaluated in combination with various methods aimed at removing non-target endosperm tissue.

| Method No. | Pericarp Removal Method | Cleanup method |
|---|---|---|
| 1 | 6% NaOH 10 min. sonication | 1% lactic acid 1 hr. soak |
| 2 | | 10 min. $H_2O$ sonication |
| 3 | | Pronase 24 hr. soak |
| 4 | 70% EtOH 24 hr. soak | 1% lactic acid 1 hr. soak |
| 5 | | 10 min. $H_2O$ sonication |
| 6 | | Pronase 24 hr. soak |
| 7 | $H_2O$ 30 min. sonication | 1% lactic acid 1 hr. soak |
| 8 | | 10 min. $H_2O$ sonication |
| 9 | | Pronase 24 hr. soak |
| 10 | 5% $H_2O_2$ 1 hr. soak | 1% lactic acid 1 hr. soak |
| 11 | | 10 min. $H_2O$ sonication |
| 12 | | Pronase 24 hr. soak |

Maize Pericarp Removal.

Pericarp DNA was isolated from seeds of 20 diverse corn hybrid families of known pedigrees, consisting of maternal, paternal and hybrid kernels. Leaf tissue from all hybrid lines was also available for use in downstream genotyping analyses. Hybrid leaf tissue DNA was extracted using the same process as for pericarp DNA samples for use as a reference data point to compare with pericarp samples of the same genetic background. Control DNA for most parents was either obtained from a maize DNA library, or where necessary, a particular parent was grown and DNA was extracted from the parent's leaf tissue using MagAttract® chemistry. "Synthetic heterozygous" leaf controls were created for each family group that contained equal concentrations of maternal and paternal DNA for comparison to hybrid pericarp DNA samples.

For DNA extraction, 5 kernels were pooled for each hybrid in each of 4 replicate wells. Thus, each hybrid analyzed was represented by a total of 20 isolated pericarps. SNP markers were selected that could identify polymorphisms across a high percentage of the analyzed hybrids.

Each set of hybrid seed was rinsed twice with di$H_2O$ to wash away all agrochemicals, dirt and other contaminants, and then patted dry. Tip caps were removed to initiate imbibition in the soaking reagent. 5% $H_2O_2$ was made fresh from a 30% stock. $H_2O_2$ oxidizes sulphydryls, amines, double bonds, and phenolic compounds, such as is present in the seed interconnecting matrix tissue (i.e., aleurone layer).

Hybrid seed was added to the 5% $H_2O_2$ solution in a 1:1 ratio (1 mL of 5% $H_2O_2$ solution for each seed). Seeds were incubated for 1 hr. at room temperature in the $H_2O_2$ solution. Pericarp were manually separated from each seed with tweezers and pooled according to the hybrid from which the seed was obtained. The pericarp were then rinsed by vortexing in a 50 mL Falcon tube of $H_2O$ for 30 sec. to remove residual $H_2O_2$, removed from the Falcon tube, and pat-dried in preparation for enzymatic treatment.

Enzymatic Treatment of Pericarp Tissue.

Pronase is a mixture of proteases derived from the extracellular fluid of *Streptomyces griseus* and is known to be highly effective in degrading a wide variety of proteins. A 10 mg/mL stock solution of Pronase was prepared in Milli-Q™ $H_2O$. A buffer solution was then prepared containing 0.1M Tris (pH 7.5) and 0.5% SDS. The buffer solution was then heated to 40° C. and the Pronase stock (10 mg/mL) was added to a final concentration of 1 mg/mL.

Following the $H_2O$ rinse, a Pronase solution (1 mg/mL) was freshly made and added to each group of pericarp in a 1:1.4 ratio of reagent to the number of seed e.g., 25 mL Pronase per 35 pericarp, which equals 3.57 mL per 5 pericarp). Samples were capped incubated for 18-24 hrs. at 55° C. After this enzymatic treatment, the Pronase was decanted into a waste reservoir, and each set of pooled pericarp was rinsed twice in di$H_2O$ (via tube inversion). Pericarp were removed from each tube, patted dry, and placed into aluminum trays to dry for 20 minutes at 55° C.

DNA Extraction.

DNA was extracted using a fully-automated modified MagAttract® DNA extraction (Qiagen, Valencia, Calif.) process carried out on a BioCel™ 1800 robot (Agilent, Santa Clara, Calif.).

After verifying that the dried pericarp samples were brittle to the touch, each set of five pericarp was broken into small pieces on weigh paper and funneled into a 1.4 mL matrix tube (3711, ThermoScientific, Waltham, Mass.) for grinding. After adding one heavy shot bead (tungsten-nickel alloy) to each tube, the rack was capped, and the samples were ground in a Genogrinder® 2010 (SPEX SamplePrep, LLC, Metuchen, N.J.) at 500 strokes/min. (1500 rpm) for about 6-10 min. (the specific grinding time varied due to differences in pericarp thickness among hybrids). After this initial grinding, the rack was uncapped and 750 µL of Buffer RLT™ (79216, Qiagen, Valencia, Calif.) was added to each tube. The rack was re-capped and ground for an additional 6 min. at 500 strokes/min.

Each rack was then centrifuged at 5,796 rcf (6,000 rpm) to pellet tissue and cell debris. Following centrifugation, each rack was placed onto a BioMek™ NX liquid handler (Beckman Coulter) for supernatant transfer into a matrix rack. Because the BioCel™ centrifuge is balanced for matrix racks that contain 300 µL of buffer, an identical volume of pericarp supernatant was transferred into the new matrix rack. A single stainless steel bead (440SS [1/8 Grade 100]; Hoover Precision Products, INC., Cumming, Ga.) was added to each well to complete the balance, and it was placed into an incubator (LiCONiC, Inc.) at room temperature to await DNA extraction. A modified version of Qiagen's MagAttract® bead-based DNA extraction chemistry was used for this purpose, modifications to the manufacturer's protocol included the elimination of Buffer RB (bead binding buffer), reduction of wash buffer and magnetic bead volumes, and shorter incubation and shake times. Completed DNA plates were stored underneath the BioCel™ instrument in a second incubator at 4° C.

Determination of DNA Yield, Purity, and Quality.

Extracted DNA was characterized by PicoGreen® quantification, Nanodrop™ (Thermo Fisher Scientific, Wilmington, Del.) quantification, and DNA visualization on an agarose gel. PicoGreen® is an intercalating dsDNA dye that does not competitively bind ssDNA, RNA, or protein. For PicoGreen® quantification, 50 µL PicoGreen® dye (P7581; Invitrogen, Carlsbad, Calif.) was added to 10 mL 1×TE buffer and mixed. 90 µL PicoGreen® dye and 10 µL pericarp DNA were added to each well of a white plate (236108; Nalge Nunc International, Rochester, N.Y.), and mixed thoroughly. A serial dilution of 0, 2.5, 5.0, and 10.0 ng/µL Lambda DNA standard (N3011L; New England BioLabs, Ipswitch, Mass.)

was also added to plate wells. Absorbance was measured on a Synergy™ 4 plate reader (BioTek, Winooski, Vt.) at 485/20 and 535/10 wavelengths, and readings (with path length correction) were exported into an Excel macro to adjust values for the dilution factor. The $R_2$ value of the standard curve was verified to range between 0.97 and 1.00, ensuring the accuracy of unknown sample calculations.

To assess the purity of the extracted pericarp DNA, 2 µL undiluted pericarp DNA from each well was added directly to each pedestal of a Nanodrop™ 8000 reader. MagAttract® AE elution buffer (Qiagen) was used to blank the instrument prior to analysis. $A_{260}/A_{280}$ and $A_{260}/A_{230}$ ratios were measured to evaluate DNA purity. The $A_{260}/A_{280}$ ratio is used to assess protein contamination in genomic DNA, and its value is between 1.8 and 2.0 for a pure sample. Values below 1.8 are indicative of protein contamination, and values above 2.0 indicate RNA contamination. The $A_{260}/A_{230}$ ratio is used to detect the presence of unwanted organic compounds (e.g., polysaccharides, phenolics, and humic acid) and guanidine salts. An uncontaminated gDNA sample will have an $A_{260}/A_{230}$ ratio around 1.8.

To assess the quality of the extracted pericarp DNA in each sample, 10 µL pericarp DNA was loaded onto a 1% agarose gel containing ethidium bromide. A 400-10,000 bp High Range molecular weight ladder (12352-019, Invitrogen) was loaded on either end of the gel for comparison, and samples were run for 12 min. in an E-Holder™ power apparatus (EH-03; Invitrogen). The DNA was visualized on a GelDoc™ XR+ imager (170-8195; Bio-Rad Laboratories, Hercules, Calif.) to identify whether wells contained high MW bands (indicating intact DNA) or low MW smears (indicating fragmented DNA).

Pericarp KASPar® SNP Genotyping.

DNA from all sources (isolated pericarp DNA, parental control DNA, hybrid leaf DNA, and synthetic heterozygous leaf control DNA) were stored at 4° C. prior to KASPar® SNP PCR analysis. A DNA plate was prepared from the extract DNA plate by adding parental controls, hybrid leaf controls, synthetic heterozygous controls, and a non-template control. The reaction mix was prepared according to Table 3A using 1× KASPar® reaction mix (KBS-1004-006; Kbioscience, Hertfordshire, UK). The DNA plates were then centrifuged at 3,000 rpm for one min. A four µL reaction mix was added to each well of a 384-well PCR plate (KB-4200BW, Kbioscience). Then, 1 µL DNA was added to each well of the PCR plate from the previously prepared DNA plate. The PCR plates were then centrifuged at 3,000 rpm for 1 min. Thermal cycling was completed using the PCR parameters in Table 3B. Following PCR, the plates were centrifuged at 3,000 rpm for 1 min., and read using a fluorescent plate reader. Data analysis was completed using Kbioscience's Lab Information Management System, KRAKEN™.

Table 3. KASPar® PCR reaction components and thermal cycling parameters used to genotype DNA extracted from maize pericarp.

TABLE 3A

Reaction mix

| Reagent | Volume (µL) |
| --- | --- |
| 2x KASPar Reaction Mix | 2.50 |
| MgCl₂ (50 mM) | 0.04 |
| Allele Specific Primer Assay Mix | 0.07 |
| H₂O | 1.39 |
| Total | 4.00 |

TABLE 3B

PCR cycling parameters

| Cycle | Cycle Temperature and Time |
| --- | --- |
| Initial Denaturation | 94° C. for 15 minutes |
| 20 cycles of Denaturation, Annealing, and Extension | 94° C. for 10 seconds |
| | 57° C. for 5 seconds |
| | 72° C. for 10 seconds |
| 22 cycles of Denaturation, Annealing, and Extension | 94° C. for 10 seconds |
| | 57° C. for 20 seconds |
| | 72° C. for 40 seconds |
| Final Extension | 72° C. for 5 minutes |

Replicate DNA extractions were performed on each set of hybrid seed, and data points were averaged to determine concentration and purity ($A_{260}/A_{280}$). Values were then compared across hybrid groups to evaluate robustness of the modified MagAttract™ DNA extraction. Table 4. Concentration (0.66-8.82 ng/µL) and purity (1.68-3.06 $A_{260}/A_{280}$) varied widely among the hybrids, due in part to seed coat size and thickness and kernel size, which affect the efficiency of grinding. Seed coat composition (fiber content) can be characterized by performing acid hydrolysis to measure cellulose content, methanolysis to determine hemicellulose content, and/or pyrolysis to calculate lignin content. This information may be used to estimate pericarp DNA yield, quality, and purity from particular plants. Though seed coat thickness cannot be easily measured, variations were noted across the 20 hybrids tested, with one hybrid representing thick pericarp and a second hybrid representing thin pericarp (data not shown). DNA yields were typically higher for samples with thicker pericarp. However, no appreciable effect was observed on KASPar® assay performance between samples from thicker pericarp and samples with thinner pericarp.

As expected, pericarp DNA yields were low as compared to leaf tissue (average leaf tissue DNA concentration was approximately 60 ng/µL per sample; data not shown). Table 5. PCR amplification methods generally require little DNA input (for example, KASPar® SNP genotyping requires about 4-6 ng per reaction). Although the yield from pericarp DNA extraction is low, this is not an issue unless high volumes of DNA are required for the analysis of numerous markers. Surprisingly, purity values for DNA extracted from isolated pericarp tissue were comparable to those measured in maize leaf tissue (data not shown).

TABLE 4

Evaluation of pericarp DNA quantity and quality among multifamily hybrid samples.

| Hybrid | Ease of Removal | Avg. Pico Conc (ng/µL) | Avg. $A_{260}/A_{280}$ |
| --- | --- | --- | --- |
| Hybrid #1 | Difficult | 1.53 | 1.74 |
| Hybrid #2 | Easy | 4.03 | 1.79 |
| Hybrid #3 | Easy | 1.72 | 1.99 |
| Hybrid #4 | Easy | 7.06 | 1.92 |
| Hybrid #5 | Easy | 6.42 | 1.85 |
| Hybrid #6 | Easy | 1.24 | 1.83 |
| Hybrid #7 | Very Easy | 8.82 | 1.80 |
| Hybrid #8 | Difficult | 0.95 | 1.77 |
| Hybrid #9 | Easy | 1.32 | 1.94 |
| Hybrid #10 | Moderate | 1.54 | 1.68 |
| Hybrid #11 | Difficult | 0.66 | 2.05 |
| Hybrid #12 | Moderate | 1.06 | 1.91 |
| Hybrid #13 | Moderate | 4.16 | 1.86 |
| Hybrid #14 | Moderate | 1.24 | 3.06 |
| Hybrid #15 | Moderate | 2.04 | 2.28 |
| Hybrid #16 | Easy | 0.74 | 1.96 |

TABLE 4-continued

Evaluation of pericarp DNA quantity and quality among multifamily hybrid samples.

| Hybrid | Ease of Removal | Avg. Pico Conc (ng/μL) | Avg. $A_{260}/A_{280}$ |
|---|---|---|---|
| Hybrid #17 | Easy | 0.84 | 2.55 |
| Hybrid #18 | Moderate | 0.91 | 1.76 |
| Hybrid #19 | Moderate | 1.69 | 1.75 |
| Hybrid #20 | Moderate | 2.10 | 2.02 |
| Hybrid #21 | Easy | 3.19 | 1.92 |
| Hybrid #22 | Easy | 0.83 | 2.05 |
| Min | | 0.66 | 1.68 |
| Max | | 8.82 | 3.06 |

As mentioned previously, 10 μL of each extracted hybrid DNA sample (×5 replicate wells) was visualized on a 1% agarose E-gel™ for quality comparison. An equal volume of extracted hybrid leaf tissue DNA was loaded alongside each set of sample replicates (when available). A low molecular weight smear of DNA was observed on the E-gel™ for all hybrid pericarp samples indicating that the DNA isolated from these samples was fragmented. The DNA which was isolated from the leaf tissue yielded intact and unfragmented DNA which was observed as a band of high molecular weight DNA. The band/smear intensity is an indicator of DNA concentration, and the intensity of the DNA present on the gel correlated with the concentration which was isolated from the different tissues. As such, the results showed that DNA yields were higher for leaf tissue preparations, and the yields from pericarp tissue varied between hybrids.

Example 3

Efficacy of Extracted Pericarp DNA

A multifamily pericarp genotyping study was conducted. The 20 DAS hybrid seed families (Table 3) in addition to the control families were analyzed using KASPar® genotyping across a panel of sixteen SNP markers. The markers selected for the analysis had a high degree of allelic variability across all families, so as to demonstrate polymorphism across a high percentage of the analyzed hybrids.

Fourteen samples of isolated pericarp DNA were genotyped across the sixteen markers for each hybrid family. Table 5. Markers that were monomorphic between parents of the hybrid being tested were noted as "Mono." The notation "Het," followed by a numerical designation, was used to describe the number of instances where pericarp DNA amplified an unexpected heterozygous pattern for markers known to represent a polymorphic locus in the family group. Hybrids that correctly genotyped with the maternal control and segregated in defined clusters for a given marker were given a passing mark (✓). Markers were designated "Fail" when the genotype of the parental lines could not be determined due to poor data quality or a lack of historical parent data.

TABLE 5

KASPar ® SNP Genotyping Summary of Multifamily Hybrid Pericarp DNA Performance.

| Hybrid | Het samples | Marker | | | | | | | |
|---|---|---|---|---|---|---|---|---|---|
| | | 2967 | 1798 | 1974 | 3796 | 4576 | 1353 | 1588 | 1656 |
| Hybrid #1 | 106 | Het-14 | Het-14 | ✓ | Mono | ✓ | Mono | Mono | Het-8 |
| Hybrid #2 | — | ✓ | ✓ | ✓ | ✓ | ✓ | ✓ | ✓ | ✓ |
| Hybrid #3 | — | Mono | Mono | ✓ | ✓ | ✓ | ✓ | ✓ | ✓ |
| Hybrid #4 | — | Mono | Mono | ✓ | Mono | Mono | Mono | Mono | ✓ |
| Hybrid #5 | 28 | ✓ | Het-14 | ✓ | ✓ | ✓ | Het-14 | ✓ | Mono |
| Hybrid #6 | — | Mono | Mono | ✓ | ✓ | Mono | ✓ | ✓ | Mono |
| Hybrid #7 | — | ✓ | Mono | ✓ | ✓ | ✓ | Mono | ✓ | Mono |
| Hybrid #8 | 24 | ✓ | Het-14 | Mono | Mono | ✓ | Het-10 | ✓ | ✓ |
| Hybrid #9 | 12 | ✓ | ✓ | Mono | ✓ | Mono | Het-12 | ✓ | ✓ |
| Hybrid #10 | — | ✓ | Mono | Mono | ✓ | FAIL | ✓ | ✓ | ✓ |
| Hybrid #11 | 14 | ✓ | ✓ | ✓ | ✓ | ✓ | Het-14 | ✓ | ✓ |
| Hybrid #12 | 5 | ✓ | ✓ | Het-5 | ✓ | ✓ | Mono | ✓ | ✓ |
| Hybrid #13 | 31 | Het-12 | Het-7 | ✓ | ✓ | Het-12 | Mono | ✓ | ✓ |
| Hybrid #14 | — | Mono | Mono | Mono | ✓ | ✓ | ✓ | ✓ | ✓ |
| Hybrid #15 | — | ✓ | ✓ | ✓ | ✓ | ✓ | ✓ | ✓ | ✓ |
| Hybrid #16 | 12 | ✓ | ✓ | ✓ | ✓ | ✓ | Mono | ✓ | ✓ |
| Hybrid #17 | — | Mono | Mono | Mono | ✓ | ✓ | ✓ | ✓ | ✓ |
| Hybrid #18 | 14 | ✓ | FAIL | Het-14 | ✓ | ✓ | Mono | ✓ | ✓ |
| Hybrid #19 | 14 | Mono | Mono | Mono | Mono | FAIL | ✓ | Mono | ✓ |
| Hybrid #20 | 12 | FAIL | Mono | ✓ | ✓ | Het-12 | Mono | Mono | ✓ |
| Hybrid #21 | — | Mono | Mono | Mono | ✓ | ✓ | Mono | ✓ | ✓ |
| Hybrid #22 | — | ✓ | ✓ | Mono | ✓ | ✓ | FAIL | ✓ | ✓ |

| Hybrid | Het samples | Marker | | | | | | | |
|---|---|---|---|---|---|---|---|---|---|
| | | 1849 | 1916 | 2021 | 2168 | 2417 | 3192 | 5034 | 5543 |
| Hybrid #1 | 106 | Het-14 | Mono | Het-14 | FAIL | Het-14 | Het-14 | Het-14 | ✓ |
| Hybrid #2 | — | ✓ | ✓ | ✓ | ✓ | ✓ | ✓ | ✓ | ✓ |
| Hybrid #3 | — | ✓ | FAIL | ✓ | ✓ | Mono | ✓ | ✓ | ✓ |
| Hybrid #4 | — | ✓ | Mono | Mono | Mono | ✓ | Mono | ✓ | Mono |
| Hybrid #5 | 28 | ✓ | Mono | ✓ | ✓ | ✓ | Mono | ✓ | ✓ |
| Hybrid #6 | — | ✓ | ✓ | ✓ | ✓ | Mono | Mono | Mono | ✓ |
| Hybrid #7 | — | ✓ | Mono | ✓ | ✓ | Mono | ✓ | ✓ | Mono |
| Hybrid #8 | 24 | ✓ | ✓ | Mono | Mono | ✓ | ✓ | ✓ | ✓ |
| Hybrid #9 | 12 | ✓ | FAIL | ✓ | ✓ | ✓ | ✓ | ✓ | ✓ |
| Hybrid #10 | — | ✓ | ✓ | ✓ | Mono | ✓ | ✓ | ✓ | Mono |

TABLE 5-continued

KASPar® SNP Genotyping Summary of Multifamily Hybrid Pericarp DNA Performance.

| Hybrid #11 | 14 | ✓ | ✓ | ✓ | ✓ | ✓ | ✓ | ✓ | ✓ |
|---|---|---|---|---|---|---|---|---|---|
| Hybrid #12 | 5 | ✓ | ✓ | ✓ | Mono | ✓ | ✓ | Mono | ✓ |
| Hybrid #13 | 31 | ✓ | Mono | ✓ | ✓ | Mono | ✓ | ✓ | Mono |
| Hybrid #14 | — | ✓ | ✓ | ✓ | ✓ | ✓ | ✓ | ✓ | ✓ |
| Hybrid #15 | — | ✓ | ✓ | ✓ | ✓ | ✓ | ✓ | ✓ | ✓ |
| Hybrid #16 | 12 | ✓ | Mono | ✓ | ✓ | Het-12 | ✓ | ✓ | ✓ |
| Hybrid #17 | — | ✓ | ✓ | ✓ | ✓ | ✓ | ✓ | Mono | ✓ |
| Hybrid #18 | 14 | ✓ | Mono | ✓ | ✓ | Mono | ✓ | ✓ | ✓ |
| Hybrid #19 | 14 | ✓ | Het-14 | ✓ | Mono | ✓ | Mono | ✓ | Mono |
| Hybrid #20 | 12 | Mono | ✓ | Mono | Mono | Mono | Mono | Mono | Mono |
| Hybrid #21 | — | ✓ | Mono | Mono | Mono | ✓ | ✓ | ✓ | Mono |
| Hybrid #22 | — | ✓ | Mono | ✓ | ✓ | ✓ | ✓ | ✓ | ✓ |

For each marker in Table 5, 14 replicate samples per hybrid were tested. Hybrid #1 and Hybrid #2 were included in the analysis. Markers that were monomorphic between the parents tested in a hybrid family were noted "Mono." Markers that amplified heterozygous alleles for a given hybrid were noted "Het" followed by the number of replicates out of 14 that amplified heterozygous alleles. Markers were noted "Fail" when the data quality was poor and historical marker data was not available to verify maternal allele amplification. Markers were given a passing score (✓) when all of the replicate wells for the hybrid tested amplified maternal alleles.

Of the 20 hybrid samples evaluated, 10 lines amplified homozygous maternal alleles. Table 5. Six of the hybrid lines displayed heterozygous amplification patterns for a single marker in at least one of the replicate pericarp wells. Hybrid #5 amplified heterozygous alleles in 14 of 14 replicate wells for markers 1798 and 1353. Hybrid #8 amplified heterozygous alleles in 14 of 14 replicate wells for marker 1798, and 10 of 14 replicate wells for marker 1353. Hybrid #13 amplified heterozygous alleles in 7 of 12 replicate wells for marker 1798, and 12 of 14 replicate wells for markers 2967 and 4576. While heterozygous genotypes observed in hybrid pericarp DNA could result from paternal allele contamination if residual endosperm/aleurone tissue was present on the inner pericarp wall and carried over into the DNA extraction process, this is an unlikely explanation, as heterozygosity was not observed across all polymorphic markers or in all replicate samples tested for those families.

Instead, heterozygous genotypes observed in pericarp DNA samples data can be attributed to KASPar® marker assay performance, an effect of pooling pericarp DNA from multiple kernels, and/or DNA quality. Markers 1798 and 1353 exhibited a high frequency of heterozygous alleles, which suggests that KASPar® marker assay performance may affect accuracy in allele calling. The particular KASPar® marker assays used were validated using high quality DNA extracted from leaf tissue, which generate higher quality metrics than those reported for pericarp DNA. To minimize or eliminate the risk that KASPar® marker assay performance may affect accuracy in allele calling, markers to be used in pericarp testing may be validated using isolated pericarp DNA prior to genotyping to identify the most robust marker panel for downstream use.

Additionally, the observation of heterozygous genotypes in pericarp DNA may be the effect of pooling pericarp DNA from multiple kernels. Segregating loci would generate individual kernels with variable genotypes and be observed as heterozygous in KASPar® SNP analyses. Genotype results from single hybrid kernels (rather than pooled DNA) for hybrids displaying heterozygous genotype patterns can be obtained to determine whether pooling of pericarp DNA from multiple kernels is responsible for observed heterozygosity.

DNA quality is another potential cause of observed heterozygosity in hybrid pericarp DNA samples. Our initial data showed no sizable differences in cellulose content among hybrids (data not shown). A commercially-available starch detection assay can also be used to quantitatively determine whether residual starch (emanating from endosperm tissue) is present on the inner wall of Hybrid #1 pericarp tissue prior to DNA extraction. If residual starch is detected, further enzymes (e.g., amylase, amyloglucosidase, etc.) may be used in addition to the non-specific protease treatment (e.g., Pronase) to gelatinize and hydrolyze the starch for disposal will be developed.

While paternal allele contamination is not suspected in the 20 hybrid families, consistent heterozygosity was observed for the control family, Hybrid #1. Because heterozygosity was consistently observed across multiple markers (in at least one replicate across 8 of the 11 polymorphic markers) in Hybrid #1, the determination of heterozygous genotypes is accurate, and paternal allele contamination may be present in the pericarp from this family. Further, the DNA yield and purity for Hybrid #1 were 1.53 ng/μL and 1.74 $A_{260}/A_{280}$, respectively, which is consistent with the 20 hybrids tested and indicates that DNA quality did not contribute to the efficacy of pericarp SNP genotyping for Hybrid #1.

The observed heterozygous allele amplification in Hybrid #1 could be due to the use of an impure source of the maternal progenitor line when hybrid seed was created. Although parental controls derived from high quality DNA were included in this study, the exact source used to create the hybrid seed is unknown. Furthermore, the breeding team that produced the Hybrid #1 line indicated that Hybrid #1 is an experimental hybrid, and that the possibility of contamination is higher than normal. If an impure source of the maternal progenitor line was used, segregation in the hybrid seed would be expected. Due to the fact that pericarp are pooled in this SNP genotyping method, any segregation would appear as heterozygosity. The ability to discriminate maternal alleles can be improved using parental controls derived from pericarp tissue (data not shown).

Embryonic-based DNA extracted from leaf tissue for Hybrid #1 was not available for use as a reference data point in the multifamily study. In initial validation assays, Hybrid #1 leaf tissue was included. However, only one hybrid plant was used to extract the leaf tissue DNA, and this does not provide enough information to determine if the parental lines were genetically pure, as it reflects only the fixed allelic state of the single hybrid plant.

Example 4

Validation of Breeding Program Results

The above-described pericarp DNA isolation and analysis method was used for the assessment of a converted maize line that was developed using a marker assisted breeding program and displayed unexpected phenotypes during the later stages of the variety development process.

The converted line, displayed shortened ears across a subset of lines during the variety finishing process. To confirm that genetic contamination was not introduced in the previous generation, or any generation since the final selections advanced into the finishing nursery from the trait introgression nursery, the method described above was used to extract pericarp DNA from a subset of materials displaying normal and undesirable phenotypes.

The pericarp DNA was then characterized using 32 SNP markers and compared to baseline genetics of the converted line, as well as phenotypic observations, to determine if correlations were present. This characterization provided no evidence of genetic variation between the short ear and normal ear plants, and the team recommended that the breeding program should proceed.

Example 5

A Use of Isolated Pericarp DNA in a Breeding Program

Pericarp DNA can be used to guide breeding practices in global geographies using competitor germplasm by inferring the putative genetics of the unknown parent and serving as a predictive tool to select additional lines that would yield similar agronomic performance.

A hybrid grain plant with an unknown maternal inbred parent is provided. Pericarp DNA is isolated from the plant, and genotyped (e.g., by PCR-based genotyping). The genotype determined thereby for the pericarp is the predicted genotype of the unknown maternal parent plant. One or more genetic markers reflected within the predicted genotype of the unknown maternal parent plant are determined to be linked to one or more traits of interest in the hybrid grain plant. A known inbred plant with a genotype having at least a subset of the linked markers is bred with an appropriate plant (e.g., the paternal parent of the hybrid grain plant with an unknown maternal inbred parent, if the paternal parent is known) to produce a second hybrid plant, wherein the second hybrid has an increased probability of having the one or more traits of interest.

A hybrid grain plant with an unknown paternal parent is provided. Pericarp DNA is isolated from the plant, and genotyped (e.g., by PCR-based genotyping). Non-pericarp DNA that comprises parental allelic information is isolated from the plant, and genotyped (e.g., by PCR-based genotyping). The genotype determined for the pericarp is compared with the genotype determined for the non-pericarp, and the allelic information in the non-pericarp genotype is the predicted genotype of the unknown paternal parent plant. One or more genetic markers reflected within the predicted genotype of the unknown paternal parent plant are determined to be linked to one or more traits of interest in the hybrid grain plant. A known inbred plant with a genotype having at least a subset of the linked markers is bred with an appropriate plant (e.g., the maternal parent of the hybrid grain plant with an unknown paternal inbred parent, if the maternal parent is known) to produce a second hybrid plant, wherein the second hybrid has an increased probability of having the one or more traits of interest.

What may be claimed is:

1. A method for isolating pericarp nucleic acid molecules from a seed sample, the method comprising:
   contacting the seed sample with hydrogen peroxide ($H_2O_2$);
   treating the seed sample with at least one enzyme selected from the group consisting of proteases, amylases, amyloglucosidases, and cellulases;
   separating pericarp tissue from other materials in the $H_2O_2$-soaked and enzyme-treated seed sample; and
   extracting nucleic acid molecules from the pericarp tissue.

2. The method according to claim 1, wherein contacting the seed sample with $H_2O_2$ comprises soaking the seed sample in an aqueous solution comprising about 5% $H_2O_2$.

3. The method according to claim 1, wherein the enzyme is a non-specific protease.

4. The method according to claim 3, wherein treating the seed sample with the non-specific protease comprises soaking the seed sample in a reaction mixture comprising about 1 mg/mL non-specific protease.

5. The method according to claim 1, wherein contacting the seed sample with $H_2O_2$ comprises soaking the seed sample in an aqueous solution comprising about 5% $H_2O_2$, and wherein treating the seed sample with at least one enzyme comprises soaking the seed sample in a reaction mixture comprising about 1 mg/mL protease.

6. The method according to claim 1, wherein extracting nucleic acid molecules from the pericarp tissue is performed utilizing a bead-based DNA extraction platform.

7. The method according to claim 1, wherein the nucleic acid molecules consist essentially of pericarp nucleic acid molecules.

8. The method according to claim 7, wherein parental nucleotide sequences are not amplified from the nucleic acid molecules by polymerase chain reaction (PCR).

9. The method according to claim 1, wherein contacting the seed sample with $H_2O_2$ comprises soaking the seed sample in an aqueous solution comprising less than about 10% $H_2O_2$.

10. The method according to claim 1, the method further comprising:
    washing the seed sample to remove associated chemicals and/or materials;
    dissecting manually the seed sample;
    sonication of the seed sample of interest;
    rinsing the seed sample so as to remove solvent and/or enzymes;
    separating released pericarp from the seed sample; and/or
    soaking the seed sample in a solvent.

11. The method according to claim 1, wherein the pericarp tissue comprises essentially no non-pericarp tissue.

12. The method according to claim 1, wherein the seed sample is a single seed.

13. The method according to claim 1, wherein the seed sample is from *Zea mays*.

14. A method for determining the matrilineage of a plant of interest having a paternal parent and a maternal parent, the method comprising:
    providing a seed sample from the plant of interest;
    contacting the seed sample with hydrogen peroxide ($H_2O_2$);
    treating the seed sample with at least one enzyme selected from the group consisting of proteases, amylases, amyloglucosidases, and cellulases;

separating pericarp tissue from other materials in the H$_2$O$_2$-soaked and enzyme-treated seed sample;

extracting nucleic acid molecules from the pericarp tissue; and genotyping the nucleic acid molecules, wherein the genotype corresponds to the genotype of the maternal parent of the plant of interest.

15. The method according to claim 14, wherein the genotype or haplotype of the maternal parent is deduced.

16. The method according to claim 14, wherein the seed sample is a single seed.

17. The method according to claim 14, wherein genotyping the nucleic acid molecules comprises amplifying nucleotide sequences from the nucleic acid molecules utilizing the polymerase chain reaction (PCR).

18. The method according to claim 14, wherein genotyping the nucleic acid molecules comprises determining allelic information at a locus that is linked to a trait of interest.

19. The method according to claim 14, wherein genotyping the nucleic acid molecules comprises determining allelic information at a locus, and comparing the allelic information with the genotype of a known second plant of interest.

* * * * *